US006623766B1

United States Patent
Tripathi et al.

(10) Patent No.: US 6,623,766 B1
(45) Date of Patent: Sep. 23, 2003

(54) PROCESS FOR INSECTICIDAL FORMULATION EFFECTIVE IN CONTROLLING MALARIAL VECTOR, MOSQUITOES

(75) Inventors: Arun Kumar Tripathi, Lucknow (IN); Veena Prajapati, Lucknow (IN); Suman Preet Singh Khanuja, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/103,352

(22) Filed: Mar. 21, 2002

(51) Int. Cl.[7] .......................... A61K 35/78; A01N 25/34
(52) U.S. Cl. ...................... 424/742; 424/405; 424/745; 424/747; 424/756
(58) Field of Search .................... 424/405, 725, 424/742, 747, 756, 745

(56) References Cited

FOREIGN PATENT DOCUMENTS

DE        10021560       * 11/2001
WO        WO 02/02065    *  1/2002

OTHER PUBLICATIONS

Bindra et al., J of Medicinal and Aromatic Plant Sciences (2000), 22: 707–709. Use of essential oils containing preparation for human protection against mosquitoes.*

Translation of DE 10021560, Quirin et al., "A Skin Care Agent with Insect Repellent Action", PTO 02–4582.*

* cited by examiner

Primary Examiner—Christopher R. Tate
Assistant Examiner—Michele C. Flood
(74) Attorney, Agent, or Firm—Thomas R. Vigil; Welsh & Katz, Ltd.

(57) ABSTRACT

The present invention relates to a new herbal synergistic formulation, comprising essential oil of medicinal plant *Foeniculum vulgare* and other plants and said formulation useful as insecticide against mosquito larvae; in addition, the formulation of the present invention has toxic action against larval stages of malarial vector, *Anopheles stephensi* due to the property attributed by the synergistic combination of essential oil of plant genus *Foeniculum vulgare* and other essential oils derived from medicinal plants.

10 Claims, No Drawings

PROCESS FOR INSECTICIDAL FORMULATION EFFECTIVE IN CONTROLLING MALARIAL VECTOR, MOSQUITOES

FIELD OF THE INVENTION

The present invention relates to a new herbal formulation, comprising essential oil of medicinal plant *Foeniculum vulgare* and other plants useful as insecticide against mosquito larvae. The formulation of the present invention has toxic action against larval stages of malarial vector, *Anopheles stephensi*. The property is attributed to the synergistic combination of essential oil of plant genus *Foeniculum vulgare* and other essential oils derived from medicinal plants.

BACKGROUND AND PRIOR ART REFERENCES

Mosquitoes are the single largest group of insects, which transmit many diseases like malaria, filaria, Japanese encephalitis and dengue throughout the world. For the management of vector mosquito population, use of chemical insecticides is now being seriously questioned due to various factors like multiple resistance to insecticides, environmental pollution, and high cost.

*Anopheles stephensi* Liston type form is a major vector of urban malaria in India (Sharma, 1996). This species essentially breeds in contained water habitats such as overhead tanks, water storage at construction sites, piped water leakages in sluice valve chambers, ornamental fountain tanks, cemented pools, wells etc. (Kalra and Sharma, 1987). Outbreaks of malaria in urban areas due to *A. stephensi* at the construction sites have been reported (Kumar et al., 1991; Adak et al., 1994). In India, control of urban malaria is carried out under urban malaria scheme (UMS) which is based on anti-larval methods. At present about 46 million population living in 29 cities is under high risk requiring accelerated urban malaria control program.

Every year, there are an estimated 300 million cases of malaria throughout the world. Mortality associated with malaria is estimated at 1.1 million deaths per year (WHO 1999) and is rising in tandem with drug resistance (WHO, 1999; Trape, et al., 1998).

Approaches to reducing the incidence of malaria have focused largely on controlling mosquito populations with chemical insecticides and by physical barrier methods (impregnated nets), or by using drugs to prevent infection with malarial parasites (Plasmodium spp).

The continued use of chemical insecticides results in the gradual building up of resistance in mosquitoes as well as in environmental pollution. Chemical insecticides are toxic to the non-target natural predators of mosquitoes, which co-exist with the mosquito larvae. Alternatively, biological control agents, such as larvivorous fish, have been successfully used under bioenvironmental methods for the persistent control of mosquito breeding (Sharma 1986).

The problems presented and created by the spraying of chemical insecticides in malaria control has made it imperative to develop alternate methods of vector control. Biocides offer many advantages over chemicals i.e., high specificity, biodegradability, safety to environment, low cost and in some cases recycling properties, these characteristics make the biocide an important and useful tool in integrated vector control program.

Most mosquito control programs aim at larval stages as a target in their breeding sites with larvicides, because adulticides may only reduce adult populations temporarily allowing for rapid upsurges within a few days. Kettle (1995) pointed out that control of immature stages of mosquitoes has traditionally been effected by the application of insecticides as solution in oils, as an emulsion, wettable powders or dusts. However, these have been achieved with the inherent risk of contamination of water used for domestic purposes especially in rural areas where this water provides excellent breeding conditions for mosquitoes. Due to the dramatic increase in resistance of mosquitoes to familiar chemicals in the absence of new compounds, better alternative means of control are sought. The urge for this has increased, especially after recent public awareness of potential hazards emanating from the widespread use of insecticides (Busvine and Pal, 1969; Curtis and Pasteur, 1981; WHO, 1987). One alternative is the use of plant extracts as botanical insecticides (Arnason et al., 1989). A considerable number of plant derivatives have been shown to be effective against a wide array of insect species (Schumutterer, 1990; Elhag et al., 1996; Wilps, 1995; Amorose, 1995), but very few have been reported for larvicidal action against mosquitoes e.g. dichloromethane extract of *Abuta grandifolia* and *Minthostachys setosa* against larvae of *Aedes aegypti*, a mosquito vector of dengu fever (Ciccia et al., 2000) and seed extract of *Atriplex canescens* against larvae of another mosquito species, *Culex quinquefasciatus* (Ouda et al., 1998).

There is no record of resistance to whole-plant extracts, possibly due to the synergistic action of many constituents: isolation and administration of a single active agent greatly facilitates the evolution of resistance in parasites (Chawira, et al., 1986) and mosquitoes. It is possible that phytotherapy produces fewer adverse effects than chemotherapy, because there are many active agents, each at a smaller dose than that required when a single agent is administered.

*Foeniculum vulgare* Mill syn. *F. capillaceum* Grilib is a aromatic herbaceous plant known locally (in India) as fennel and used as culinary spice. The fruits are aromatic, stimulant and carminative. Official pharmacopoeias of various countries throughout the world list this plant for use in diseases of the chest, spleen and kidney. Fennel is a constituent of liquorice powder and preparation for allaying gripping. *F. vulgare* has been reported to exhibit many pharmacological effects including antibacterial activity (Ruberto et al., 2000) and toxicity towards stored grain insects (Kim and Ahn, 2001). It is useful in infantile colic and flatulence (Purthi, 1976). In spite of considerable pharmacological studies carried out world wide on *F. vulgare* fruits survey of scientific literature showed that the essential oil of *F. vulgare* has not been evaluated against insect vectors of public health like mosquitoes. The applicants have carried out preliminary experiments on essential oil of the fennel fruit (*Foeniculum vulgare*) to explore whether it possesses any toxic and/or behavior modifying effects towards malarial vector, *A. stephensi* (Liston).

Hitherto known insecticides to control of malarial vector at larval stage are malariol oil, temephos and fenthion, and are being commonly used in anti-larval operations but all these compounds are also toxic to co-existing beneficial organisms.

Hitherto known some plant products have been demonstrated to be effective against mosquitoes (Wilps, 1995; Elhag, 1996). Example include *Syzygium aromaticum* (L.) (Hassanali et al., 1990), *Curcuma raktakanda* (Latha and Ammini, 2000), *Hydrocotyle jaranica* Thunb.

(Venkatachalam and Jebanesan, 2001), and *Azardirachta indica* A. Juss. (Elhag et al., 2001; Prasad, et al., 2001).

During the course of our research, in an attempt for preparing insecticides from natural products, the applicants have found that the essential oil of a medicinal plant, *Foeniculum vulgare* and other plant either singly or in combination can be employed for controlling mosquito, *Anopheles stephensi*.

The technical ingredient used in the present invention, essential oil of *F. vulgare* is reported in the literature for toxicity towards insect-pest but not towards *A. staphensi*.

OBJECTS OF THE INVENTION

The main object of present invention is therefore to provide a composition of essential oils as an herbal larvicide useful in killing mosquito larvae and obviates the drawbacks as detailed above.

Another object of the present invention is to provide a composition of the plant essential oils as an herbal formulation useful as larvicide for the control of mosquito larvae, which is safe, cheap, biodegradable, environmentally friendly, without any residual effect and commercially viable.

Another object of the invention is to provide a composition, which is miscible with water enabling it to be compatible with other microorganism present in water.

SUMMARY OF THE INVENTION

Accordingly the present invention provides a composition useful as an insecticide or larvicide, particularly against mosquito larvae which comprises blending the essential oil extracted from the plant genus *Foeniculum vulgare* with one or other essential oils of medicinal plants.

The basis for which the invention has been developed is due to our finding that when essential oil of *Foeniculum vulgare* is mixed with one or other essential oils of medicinal plants; the resultant composition develops insecticidal property, which is especially active against mosquito larvae. The water miscibility as an additional advantage with the use of essential oil makes the invention more superior than commercially available insecticides which only floats on the water surface thereby cause suffocation to other water inhabiting organisms by depleting the oxygen level in the water. Accordingly, the composition is useful as larvicide for the control of mosquitoes.

DETAILED DESCRIPTION OF THE INVENTION

Accordingly, the present invention provides a novel synergistic herbal insecticidal formulation against mosquito larvae, said formulation comprising:

(i) essential oil derived from plant *Foeniculum vulgare* 0.01 to 2.6 wt. %, (ii) essential oil(s) derived from one or more plant sources 0.01 to 2.6 wt. %, (iii) emulsifier or combination of emulsifier 0.01 to 3.8 wt. % and, (iv) balance water as a carrier or diluent.

One more embodiment of the invention relates to a synergistic formulation, wherein the essential oil(s) from other plant(s) is/are selected from plants belonging to families Apiaceae, Geraniaceae, Lamiaceae, Meliaceae, Myrtaceae, Poaceae and Zingiberaceae.

Another embodiment, the essential oils used can also be extracted from different plants selected from *Eucalyptus citriodoora, Foeniculum vulgare, Mentha spicata* var. *viridis, Mentha arvensis, Mentha piperita, Ocimum basilicum*, Cymbopogon species, *Pelargonium graveolens* and/or *Zingiber officinale* or mixtures thereof.

Still another embodiment, emulsifier used for preparing the formulation may be ionic, non-ionic or mixtures thereof, selected form group consisting of Soya lecithin, Tween-20, Tween-80 and Triton-X.

Yet, another embodiment of the invention relates to the activity of the formulation against mosquito larvae of various mosquito species selected from *Aedes aegyptii, Anopheles stephensi, Anopheles quadrimaculatus* and Culex species.

Yet another embodiment of the invention relates to the essential oils which are selected from *Foeniculum vulgare* in the range of 0.01 to 2.6 wt. %, *Mentha spicata* var. *viridis* in the range of 0.01 to 2.6 wt. %, and *Zingiber officinale* in the range of 0.01 to 2.6 wt. %.

Yet another embodiment of the invention relates to ratio of essential oils of plants *Foeniculum vulgare: Mentha spicata* var. *viridis:Zingiber officinale* which is in the range of 1–7: 1–5: 1–7.

Yet another embodiment, preferred ratio of essential oils of plants *Foeniculum vulgare: Mentha spicata* var. *viridis:Zingiber officinale* used is in the range of 3–7: 1–5: 3–7.

Yet another embodiment, the said formulation is having synergistic activity against the mosquito, wherein mean mortality of mosquito larvae is up to 94%.

In another embodiment of the invention provides a herbal formulation useful as insecticide against malarial vector, mosquito which comprises of 0.01 wt. % to 2.6 wt. % of essential oil derived from plant genus *Foeniculum vulgare* and 0.01 wt. % to 2.6 wt. % of one or more essential oils of plants and 0.01 wt. % to 3.8 wt. % of tween-80 or combinations thereof belonging to plant family Apiaceae, Geraniaceae, Lamiaceae, Myrtaceae, Meliaceae, Poaceae and Zingiberaceae.

In an embodiment of present invention, has several components which include formulation in the form of liquid which is fit for use in water logging conditions and can be used any time by mixing it with water and tween-80, an emulsifying agent. It is non-toxic to human beings, parasite and predators. The present invention thereby provides for the preparation of an insecticidal formulation which when used provides complete killing of mosquito larvae. The response is the result of insecticidal property of the composition-enabling killing of target insects.

The preferred composition of the present invention consists of essential oil of plant genus *Foeniculum vulgare, Mentha spicata viridis* and *Zingiber officinale* and Tween-80 purchased from Hi-Media, Mumbai. The amount of these components may range from 1:1:1 to 3:5:7.

The invention is illustrated by the following examples, which should not be construed to limit the scope of the present invention.

EXAMPLES

Example-1

Essential oil (0.1 ml) obtained from plant genus *Foeniculum vulgare* was first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the got test solution of each concentration. Single vial with one larva was used in one replication. Thus a total of 50 insects were used in fifty replications. Mortality data for mosquito larvae were recorded after 24 hours.

It was observed that essential oil from *Foeniculum vulgarea* caused 56.0% mortality at 0.01% concentration under laboratory conditions.

Example-2

Essential oil (0.1 ml) obtained from plant genus *Mentha spicata* var. *viridis* was first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that essential oil from *Mentha spicata viridis* caused 20.0% mortality at 0.01% concentration under laboratory conditions.

Example-3

Essential oil (0.1 ml) obtained from plant genus *Zingiber officinale* was first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that essential oil from *Zingiber officinale* caused 40.0% mortality at 0.01% concentration under laboratory conditions.

Example-4

Tween-80 purchased from Hi-Media, Mumbai, India, an emulsifying agent (0.1-ml) of 0.001% concentration was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that Tween-80 caused 0.0% mortality at 0.01% concentration under laboratory conditions.

Example-5

This example demonstrates the process of making herbal formulation based on results obtained in Examples 1–4.

Essential oil (0.05 ml each) obtained from plant genus *Foeniculum vulgare* and *Mentha spicata* var. *viridis* were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oil (0.05 ml) obtained from plant genus *Foeniculum vulgare* and essential oil of (0.05 ml) obtained from plant genus *Mentha spicata* var. *viridis* (1:1) caused 60.0% mortality at 0.01% concentration under laboratory conditions.

Example-6

This example demonstrates the process of making herbal formulation based on results obtained in Examples 1–4.

Essential oil (0.05 ml each) obtained from plant genus *Foeniculum vulgare* and *Zingiber officinale* were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oil (0.05 ml) obtained from plant genus *Foeniculum vulgare* and essential oil of (0.05 ml) obtained from plant genus *Zingiber officinale* (1:1) caused 72.0% mortality at 0.01% concentration under laboratory conditions.

Example-7

This example demonstrates the process of making herbal formulation based on results obtained in Examples 1–4.

Essential oil (0.05 ml each) obtained from plant genus *Mentha spicata* var. *viridis* and *Zingiber officinale* were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oil (0.05 ml) obtained from plant genus *Mentha spicata* var. *viridis* and essential oil of (0.05 ml) obtained from plant genus *Zingiber officinale* (1:1) caused 52.0% mortality at 0.01% concentration under laboratory conditions.

Example-8

This example demonstrates the process of making herbal formulation based on results obtained in Examples 1–4.

Essential oil (0.033 ml each) obtained from plant genus *Foeniculum vulgare, Mentha spicata* var. *viridis* and *Zingiber officinale* were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oils (0.033 ml each) obtained from plant genus *Foeniculum vulgare, Mentha spicata* var. *viridis* and *Zingiber officinale* (1:1:1) caused 65.0% mortality at 0.01% concentration under laboratory conditions.

Example-9

This example demonstrates the process of making herbal formulation based on results obtained in Examples 1–4.

Essential oils obtained from plant genus *Foeniculum vulgare* (0.02 ml), *Mentha spicata* var. *viridis* (0.06 ml) and *Zingiber officinale* (0.02 ml) were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oils obtained from plant genus *Foeniculum vulgare* (0.02 ml), *Mentha spicata* var. *viridis* (0.06 ml) and *Zingiber officinale* (0.02 ml) (1:3:1) caused 50% mortality at 0.01% concentration under laboratory conditions.

Example-10

This example demonstrates the process of making herbal formulation based on results obtained in Examples 1–4.

Essential oils obtained from plant genus *Foeniculum vulgare* (0.043 ml), *Mentha spicata* var. *viridis* (0.014 ml) and *Zingiber officinale* (0.043 ml) were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oils obtained from plant genus *Foeniculum vulgare* (0.043 ml), *Mentha spicata* var. *viridis* (0.014 ml) and *Zingiber officinale* (0.043 ml) (3:1:3) caused 78.0% mortality at 0.01% concentration under laboratory conditions.

Example-11

This example demonstrates the process of making herbal formulation based on results obtained in Examples 1–4.

Essential oils obtained from plant genus *Foeniculum vulgare* (0.021 ml), *Mentha spicata* var. *viridis* (0.033 ml) and *Zingiber officinale* (0.046 ml) were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oils obtained from plant genus *Foeniculuni vulgare* (0.021 ml), *Mentha spicata* var. *viridis* (0.033 ml) and *Zingiber officinale* (0.046 ml) (3:5:7) caused 84.0% mortality at 0.01% concentration under laboratory conditions.

Example-12

This example demonstrates the process of making herbal formulation based on results obtained in Examples 1–4.

Essential oils obtained from plant genus *Foeniculum vulgare* (0.033 ml), *Mentha spicata* var. *viridis* (0.021 ml) and *Zingiber officinale* (0.046 ml) were first mixed with Tween-80 (0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oils obtained from plant genus *Foeniculum vulgare* (0.033 ml), *Mentha spicata* var. *viridis* (0.021 ml) and *Zingiber officinale* (0.046 ml) (5:3:7) caused 82.0% mortality at 0.01% concentration under laboratory conditions.

Example-13

This example demonstrates the process of making herbal formulation based on results obtained in Examples 1–4.

Essential oils obtained from plant genus *Foeniculum vulgare* (0.046 ml), *Mentha spicata* var. *viridis* (0.033 ml) and *Zingiber officinale* (0.021 ml) were first mixed with Tween-80-(0.1 ml) of 0.001% concentration and then the mixture was dissolved in water to make the solution of 0.01% concentration. This solution was tested against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that combination of essential oils obtained from plant genus *Foeniculum vulgare* (0.046 ml),

*Mentha spicata* var. *viridis* (0.033 ml) and *Zingiber officinale* (0.021 ml) (7:5:3) caused 86.0% mortality at 0.01% concentration under laboratory conditions.

Example-14

This example demonstrate the efficacy of a synthetic chemical, β-Asarone purchased from M/s SIGMA, USA and taken as standard. It was tested at 0.0016% concentration against mosquito (*Anopheles stephensi*) larvae in the laboratory.

Standard WHO test (WHO, 1981) was employed with slight modification in the test procedure. A single fourth-stage larva was put into each of fifty vials containing 5 ml of the test solution of each concentration. Single vial with one larva was used in one replication. Thus a total of 50 insects were used in fifty replications. Mortality data for mosquito larvae were recorded after 24 hours.

It was observed that β-Asarone caused 100.0% mortality under laboratory conditions.

The summary of results of above examples (1–14) is given in Table-1.

TABLE 1

Killing effect of essential oils or their mixtures against mosquito *Anopheles stephensi* larvae

| Examples | Ratio | Mean % mortality after 24 hours |
| --- | --- | --- |
| 1 | — | 56 |
| 2 | — | 20 |
| 3 | — | 40 |
| 4 | — | 0 |
| 5 | 1:1 | 60 |
| 6 | 1:1 | 72 |
| 7 | 1:1 | 52 |
| 8 | 1:1:1 | 65 |
| 9 | 1:3:1 | 50 |
| 10 | 3:1:3 | 78 |
| 11 | 3:5:7 | 94 |
| 12 | 5:3:7 | 82 |
| 13 | 7:5:3 | 86 |
| 14 | — | 100 |

It is observed from the above Table-1 that essential oil of *Foeniculuin vulgare* when mixed with essential oils of other plants like *Mentha spicata* var. *viridis* and *Zingiber officinale* at varying degree of ratio, resulted into varying degree of killing effect towards mosquito larvae.

Advantages

Accordingly, it can be observed that the composition of the present invention is not a mere admixture having the aggregate properties of all the ingredients but act as a synergistic mixture resulting in enhanced activity with sustained effect.

The advantage of present invention is that being plant based formulation, it is Eco-friendly, non-toxic to organisms co-existing with mosquito larvae under natural habitats and sustainable.

Another advantage of the present invention is that, the composition is cheaper and more effective than other plant products reported like leaf extracts of *Ricinus communis* and *Azadirachta indica*, and due to its water miscibility as an additional property of the formulation, thereby reducing the harmful effect on other mosquito larvae co-inhabiting loving organisms.

REFERENCES

Adak, T., Batra, C. P., Mittal, P. K. and Sharma, V. P. (1994). Epidemiological study of malaria outbreak in hotel construction site of Delhi. Indian J. Malariol., 31: 126–131.

Amorose, T. (1995). Larvicidal efficacy of neem (*Azadirachta indica* A. Juss) oil and defatted cake on Culex quinquefasciatus Say. Geobios (Judhpur), 22:169.

Arnason, J. T., Philogene, R. J. R., and Morand, P. (1989). Insecticides of Plant Origin. ASC Symp. Ser. 387, Washington, D.C.

Busvine, J. R., and Pal, R. (1969). Impact of insecticide-resistance on control of vectors and vector-borne diseases. Bull. WHO 40, 731.

Chawira, A. N. et al. (1986). Qinghaosu resistance in rodent malaria Trans. R. Soc. Trop. Med. Hyg. 80, 477–480.

Ciccia, G., Coussio, J. and Mongelli, E. (2000). Insecticidal activity against *Aedes aegypti* larvae of some medicinal South American plants. Journal of Ethnopharmacology, 72: 185–189.

Curtis, C. F., and Pasteur, N. (1981). Organophosphate resistance in vector populations of the complex of *Culex pipiens* (Diptera: Culicidae). Bull. Entomol. Res. 71, 153.

Elhag, E. A., Harraz, F. M., Zaitoon, A. A., and Salama, A. K., 1996. Evaluation of some wild herb extracts for control of mosquitoes, (Diptera: Culicidae). J. King Saud University, Agric. Sci. 8, 135.

Elhag, E. A., Rahman, Abd-El, Nadi, H. E., and Zaitoon, A. A. 2001. Effects of methanolic extracts of neem seeds on egg hatchability and larval development of *Culex pipiens* mosquitoes. Indian Veterinary J. 78, 199–201.

Hassanali, A., Lwande, W., Ole-Sitayo, N., Moreka, L., Nokoe, S., and Chapya, A., 1990. weevil repellent constituents of *Ocimum suava* leaves and *Eugenia caryophyllata* cloves used as grain protectants in parts of Eastern Africa. Discovery and Innovations 2,91.

Kalra, N. L. and Sharma, G. K. (1987). Malaria control in Delhi- past, present-and future. J. Com. Dis., 19: 91–116.

Kettle, D. S. (1995). Medicinal and Veterinary Entomology, $2^{nd}$ edn. CAB Int.

Kim, D. H., Ahn, Y. J., 2000. Contact and fumigant activities of constituents of *Foeniculum vulgare* fruit against three coleopteran stored-product insects. Pest Management Science 57, 301–306.

Kumar, A., Sharma, V. P. and Thavaselvam, D. (1991). Malaria related to constructions in Panaji. Indian J. Malariol., 28: 219–225.

Latha, C., Ammini, J., 2000. *Curcuma raktakanda* is a potential larvicide for mosquito control. Parmaceutical Biology 38, 167–170.

Ouda, N., Al-Chalabii, B. M., Al-Charchafchi, F. M. R. and Mohsen, Z. H. (1998). Insecticidal and ovicidal effects of the seed extract of *Atriplex canescens* against *Culex quinquefasciatus*. Pharmaceutical Biology, 36:69–71.

Prasad, S. M, Singh, D. Zeeshan, M. 2001. Toxicity of aqueous extract of *Azadirachta indica* against larvae of mosquito *Anopheles stephensi*. J. Experimental Zoology India, 4, 75–79.

Purthi, J. S. 1976. Spices and Condiments. P. 114–118. National Book Trust, New Delhi, India.

Ruberto, G., Baratta, M. mT., Deans, S. G., Dorman, H. J. D., 2000. Antioxidant and antimicrobial activities of *Foeniculum vulgare* and *Crithmum maritimum* essential oils. Planta Medica 66, 687–693.

Sharma, V. P. (1986). Malaria: Eradicating mosquitoes without insecticides. Gujarat shows the bioenvironmental way. Sci. Age. 4(8): 49–54.

Sharma, V. P. (1996). Re-emergence of malaria in India. Indian J. Med. Res., 103: 26–45.

Schumutterer, H. (1990). Properties and potential of natural pesticides from the neem tree, *Azadirachta indica*. Annu. Rev. Entomol. 35: 271.

Trape, J. F. et al. (1998). Impact of chloroquine resistance on malaria mortality. C.R. Acad. Sci. 321, 689–697.

Venkatachalam, M. R., and Jebanesan, A. 2001. Larvicidal activity of *Hydrocotyle jaranica* Thunb. (Apiaceae) extract against *Culex quinquefasciatus*. J. Experimental Zoology India, 4, 99–101.

WHO (1981). Instruction for determining the susceptibility or resistance of mosquito larvae to insecticide. WHO/VBC/81-807.

WHO (1987). Tropical Disease Research. A Global Partnership Eight Programme Report: the first Ten Years with Highlights of the 1985–1986 Biennium. Ed. By J. Maurice, and A. M. Pearce, UNDP/World Bank/WHO, TDR, Genevea.

WHO (1999). The World Health Report 1999, WHO.

Wilps, H. (1995). Effects on viruses and organism: Effect by order of Insecta: Insects: Diptera: mosquitoes and flies. In, The Neem Tree: *Azadirachta indica* A. Juss. And Other Meliaceous Plants: Source of Unique Natural Products for Integrated Pest Management, Medicine, Industary and Other Purposes, ed. By H. Schumutterer, VCH Publishers, New York.

What is claimed is:

1. A herbal insecticidal formulation for use in killing mosquito larvae, said formulation comprising:
   (a) an essential oil in the range of 0.01 to 2.6 percent by weight derived from the plant *Foeniculum vulgare*,
   (b) at least an additional essential oil in the range of 0.01 to 2.6 percent by weight derived from one or more other plant sources,
   (c) at least an emulsifier in the range of 0.01 to 3.8 percent by weight, and
   (d) the balance quantity being water as a carrier or diluent.

2. The formulation as claimed in claim 1, wherein (b), the essential oil of other plants is selected from plants belonging to the families Apiaceae, Geraniaceae, Lamiaceae, Meliaceae, Myrtaceae, Poaceae, Zingiberaceae or mixtures thereof.

3. The formulation as claimed in claim 1, wherein (b), the essential oils used is obtained by extraction of plants selected from *Eucalyptus citriodora, Mentha spicata* var. *viridis, Mentha arvensis, Mentha piperita, Ocimum basilicum,* Cymbopogon species, *Pelargonium graveolens* and/or *Zingiber officinale* or mixtures thereof.

4. The formulation claimed as in claim 1, wherein (C), the emulsifying agent is ionic, non-ionic or mixtures thereof.

5. The formulation as claimed in claim 1, having an effect in killing mosquito larvae of various mosquito species selected from the group consisting of *Aedes aegyptii, Anopheles stephensi, Anopheles quadrimaculatus* and Culex spp.

6. The formulation as claimed in claim 1, wherein the essential oils used are in the range of 0.01 to 2.6 percent by weight of *Foeniculum vulgare*, 0.01 to 2.6 percent by weight of, *Mentha spicata* var. *viridis*, in the range of 0.01 to 2.6 percent by weight of *Zingiber officinale* and/or mixtures thereof.

7. The formulation as claimed in claim 1, wherein the ratio of essential oils of plants *Foeniculum vulgare:Mentha spicata* var. *viridis:Zingiber officinale* is in the range of 1–7:1–5:1–7.

8. The formulation as claimed in claim 1, wherein the ratio of if essential oils of plants *Foeniculum vulgare:Mentha spicata* var. *viridis:Zingiber officinale* is in the range of 3–7:1–5:3–7.

9. The formulation as claimed in claim 1, having an effect in killing mosquito larvae whereby the mortality of mosquito larvae being treated is up to 94%.

10. The formulation as claimed in claim 1 wherein the emulsifying agent is selected from the group consisting of soya lecithin, polyoxyethylene esters, ethers of sorbitol and compounds belonging to the octoxynol series.

* * * * *